United States Patent [19]
Kaminsky

[11] Patent Number: 5,526,808
[45] Date of Patent: Jun. 18, 1996

[54] METHOD AND APPARATUS FOR NONINVASIVELY DETERMINING HEMATOCRIT

[75] Inventor: Allan L. Kaminsky, Park City, Utah

[73] Assignee: Microcor, Inc., Salt Lake City, Utah

[21] Appl. No.: 425,404

[22] Filed: Apr. 20, 1995

Related U.S. Application Data

[63] Continuation of Ser. No. 298,795, Aug. 31, 1994, abandoned, which is a continuation of Ser. No. 114,131, Aug. 30, 1993, abandoned, which is a continuation of Ser. No. 592,851, Oct. 4, 1990, abandoned.

[51] Int. Cl.$^6$ .............................. A61B 5/00; G06F 159/00
[52] U.S. Cl. .................... 128/632; 128/691; 128/693; 128/637; 128/734
[58] Field of Search ............................ 364/709, 710; 128/632, 633, 637, 691, 693, 734

[56] References Cited

U.S. PATENT DOCUMENTS

| | | | |
|---|---|---|---|
| 3,828,260 | 8/1974 | Underwood | 328/151 |
| 3,835,839 | 9/1974 | Brown | 128/2.05 F |
| 3,835,840 | 9/1974 | Mount | 128/693 |
| 3,871,359 | 3/1975 | Pacela | 128/693 |
| 3,994,284 | 11/1976 | Voelker | 128/2.05 F |
| 4,047,205 | 9/1977 | Grosskopf | 358/107 |
| 4,086,631 | 4/1978 | Vick | 364/416 |
| 4,738,655 | 4/1988 | Brimhall et al. | 494/10 |
| 4,835,477 | 5/1989 | Polaschegg et al. | 324/439 |
| 4,887,458 | 12/1989 | Baker et al. | 73/61.1 R |
| 4,909,261 | 3/1990 | Rothenberg | 128/734 |
| 5,040,538 | 8/1991 | Mortazavi | 128/633 |
| 5,040,539 | 8/1991 | Schmitt et al. | 128/633 |
| 5,101,825 | 4/1992 | Graveinstein et al. | 128/633 |
| 5,203,344 | 4/1993 | Scheltinga et al. | 128/734 |
| 5,246,002 | 9/1993 | Prosser | 128/633 |
| 5,246,003 | 9/1993 | Delongzor | 128/633 |
| 5,277,181 | 1/1994 | Mendelson et al. | 128/633 |
| 5,372,136 | 12/1994 | Steuer et al. | 128/633 |

OTHER PUBLICATIONS

"Noninvasive Measurement of Hematocrit by Electrical Admittance Plethysmography Technique," Yamakoshi, et al., *IEEE Transactions on Biomedical Engineering*, vol. BME-27, No. 3, Mar. 1980.

"Dual-Channel self-balancing impedance plethysmegraph for Vascular Studies," Arenson, et al., Med. Biol. Eng & Comput., 1981, 19, 157–164.

(List continued on next page.)

*Primary Examiner*—Gail O. Hayes
*Assistant Examiner*—Frantzy Poinvil
*Attorney, Agent, or Firm*—Trask, Britt & Rossa

[57] ABSTRACT

A method and apparatus for noninvasively determining hematocrit utilizing the frequency dependent electrical impedance characteristics of whole blood by electrically stimulating a patient body portion containing a pulsatile vascular compartment with a constant current source at two selected frequencies, one of which is high enough that the capacitive nature of erythrocytes will significantly affect the magnitude of the impedance of the blood. Sensed voltage across the stimulated body portion at the two frequencies is representative of the corresponding magnitudes, and the method further includes detecting the signal envelopes of the sensed voltages, isolating and converting the pulsatile components of the signal envelopes to the digital domain, normalizing each isolated converted pulsatile component against the voltage baseline of its carrier waveform and creating a ratio of the normalized isolated pulsatile components representative of the patient's hematocrit. The ratio is indexed to a look-up table constructed from clinical studies correlating such ratios at the two selected frequencies to hematocrit, and the hematocrit corresponding to the created ratio is displayed. A plurality of ratios of sets of time-matched pulsatile component segments are created and averaged using a weighted averaging technique which more heavily weights ratios created from more significant segment sets, the weighted ratio average being correlated to hematocrit via the look-up table.

30 Claims, 4 Drawing Sheets

OTHER PUBLICATIONS

"Impedance Cardiography and Electrical Proportion of Blood," Visser, et al., Proceedings of the Vth ICEBI, Aug. 1981, Tokyo.

"Differential impedance Plethysmography for measuring thoracic impedancer," Meijer, et al., Med. & Biol. Eng. & Comput., 1982, 20, 187–194.

"Simple design for an impedance plethysmograph," Swanson, et al., Med. & Biol. Eng. & Comput., 1982, 20, 461–466.

"Errors in four–electrode impedance plethyamography," Swanson et al., Med. & Biol. Eng. & Comput., 1983, 21, 674–680.

"Conductmetric experiment to assay the hemaglobin content of blood," Neelakanswaky, et al., Med & Biol. Eng. & Comput., 1984, 22, 367–370.

"Microprocessor–based system for measurement of electrical impedance during haemodialysia and in postoperative care," Goovaerta, et al., Med. & Biol. Eng. & Comput., 1988, 26, 75–80.

"Pulse Oximetry," Tremper et al., Medical Intelligence Article, Anesthesiology 70:98–108, 1989.

"Measurement of transcellular fluid shift during haemodialysis," Meijer, et al. Med. & Biol. Eng. & Comput., 1989, 27, 147–151.

"Two–frequency impedance plethyomoraph real and imaginary parts," Lozano, et al. Med. & Biol. Eng. & Comput. 1990, 28, 38–42.

*EXAR Databook*, 1987, pp. 6–62 through 65, 11–68 through 71.

"Noninvasive Measurement of Hematocrit by Electrical Admittance Plethysmography Technique," Yamakoshi, et al., *IEEE Transactions on Biomedical Engineering*, vol. BME–17, No. 3 Mar. 1980.

"Dual–channel self–balancing impedance plethysmegraph for vascular studies," Arenson, et al., Med. & Biol. Eng. & Comput., 1981, 19, 157–164.

"Impedance Cardiography and Electrical Properties of Blood," Visser, et al., Proceedings of the Vth ICE BI, Aug. 1981, Tokyo.

"Differential impedance Plethysmography for measuring thoracic impedances," Meijer, et al., Med. & Biol. Eng. & Comput., 1982, 20, 187–194.

"Simple design for an impedance plethysmograph," Swanson, et al., Med. & Biol. Eng. & Comput., 1982, 20, 461–46.

"Errors in four–electrode impedance plethysmography," Swanson et al., Med. & Biol. Eng. & Comput., 1983, 21, 674–680.

"Conductmetric experiment to assay the hemaglobin content of blood," Neelakantawaky, et al., Med. & Biol. Eng. & Comput., 184, 22, 367–370.

"Microprocessor–based system for measurement of electrical impedance during haemodialysis and in pestoperative care,".

Goovaerts, et al., Med. & Biol. Eng. & Comput., 1988, 26, 75–80.

"Pulse Oximetry," Tremper et al., Medical Intelligence Article, Anesthesiology 70:98–108, 1989.

"Measurement of transcellular fluid shift during haemodialysia," Meijer, et al. Med. & Biol. Eng. & Comput., 1989, 27, 147–151.

"Two–frequency impedance plethyomograph real and imaginary parts," Lozano, et al. Med. Biol. Eng. & Comput. 1990, 28, 38–42.

*EXAR Databook*, 1987, pp. 6–62 through 65, 11–68 through 71.

Fig. 6 ns of application Ser. No. 08/298,795
filed Aug. 31, 1994, now abandoned, which is a continuation
of application Ser. No. 08/114,131 filed Aug. 30 1993,
abandoned, which is a continuation of application Ser. No.
07/592,851 filed Oct. 4 1990, now abandoned.

BACKGROUND OF THE INVENTION

The present invention relates generally to determination of the Packed Cell Volume or relative volume percent of erythrocytes, also known as the hematocrit, of whole blood, and more specifically to a method and apparatus for making such determination noninvasively.

Hematocrit is traditionally obtained by acquiring a patient blood sample from a vein via syringe, or by use of a capillary tube from a finger stick, or puncture. The blood, contained in an elongated vessel, is then centrifuged and the height percentage of the column of blood in the vessel which is solid represents the hematocrit.

More recently, hematocrit has been obtained by the use of elaborate and expensive cell counting laboratory instruments which are also used to provide differentiations of white blood cells, platelets, etc. However, as with the centrifuge method, the blood must be invasively removed from the patient for analysis.

In the course of routine medical procedures, such as the daily blood work performed in hospitals, the necessity of obtaining blood samples from patients and then centrifuging or otherwise analyzing the drawn blood presents no great inconvenience, as the volume of samples is large (warranting expensive automated equipment) and the time delay in obtaining results from a laboratory is generally acceptable. However, in catastrophic situations such as are encountered in emergency rooms and shock trauma units, as well as in the course of surgical procedures wherein blood loss is probable, the hematocrit determination apparatus and methodology of the prior art are markedly deficient.

In the foregoing environments there may be no time to draw blood, and in fact it may be impossible to identify a vein from which to draw it. Drawing blood intermittently during surgical procedures is inconvenient if not impractical, and analyzing periodic samples is time and labor intensive. Moreover, hematocrit may vary and drop at such an accelerated rate from unobserved blood loss that by the time the emergency or surgical personnel are belatedly made aware of a problem by laboratory personnel, the patient may be in acute difficulty or even deceased.

It has been proposed to measure hematocrit noninvasively, as noted in "Noninvasive Measurement of Hematocrit by Electrical Admittance Plethysmography Technique", *IEEE Transactions of Biomedical Engineering*, Vol. BME-27, No. 3, Mar. 1980 pp. 156–161. However, the methodology described in the foregoing article involves submerging an extremity, such as a finger, in an electrolyte (NaCl solution) and varying the electrolyte concentration to compensate for pulsatile electrical admittance variations by matching the electrolyte resistivity to that of the blood in the extremity; the resistivity of the electrolyte is then determined in a resistivity cell, and converted to a hematocrit value via a nonlinear least-squares regression calibration curve generated by matching centrifuged hematocrit for various erythrocyte concentrations to resistivity data previously taken directly from blood resistivity measurements of the same specimens. Aside from being unwieldy to employ in an emergency or operating room environment, to the inventor's knowledge the technique as described in the referenced article has never been followed up or verified by further research, or employed in practice.

A measurement technique termed "impedance plethysmography", or using impedance techniques to obtain a waveform, is conceptually rooted in biomedical antiquity. Medical literature abounds with vascular studies, respiration studies and attempts to determine cardiac output (the actual volume of blood flowing from the heart) by impedance techniques. None of these techniques has been proven to work particularly well, although there have been attempts at commercial instruments based on the concept. A variant of impedance plethysmography, however, electrically models intracellular as well as an extracellular tissue components and employs a comparison of measurements of tissue impedance responsive to applied electrical currents at two frequencies to quantify the intracellular and extracellular tissue components. While not directly related to the problem solved by the present invention, the electrical tissue model is useful to an understanding thereof.

In recent years, a technique known as pulse oximetry has been employed to measure blood oxygenation during induction of general anesthesia. While pulse oximetry does not provide an hematocrit indication, one may consider it helpful to an understanding of the method and apparatus of the present invention. Pulse oximetry relies upon the fact that the light absorbance of oxygenated hemoglobin and that of reduced hemoglobin differ at two wavelengths of light (generally red and near infrared) employed in an oximeter, and that the light absorbances at both frequencies have a pulsatile component which is attributable to the fluctuating volume of arterial blood in the patient body portion disposed between the light source and the detector of the oximeter. The pulsatile or AC absorbance response component attributable to pulsating arterial blood is determined for each wavelength, as is the baseline or DC component which represents the tissue bed absorbances, including venous blood, capillary blood and nonpulsatile arterial blood. The AC components are then divided by their respective DC components to obtain an absorbance that is independent of the incident light intensity, and the results divided to produce a ratio which may be empirically related to $SaO_2$, or oxygen saturation of the patient's blood. An excellent discussion of pulse oximetry may be found in "Pulse Oximetry", by K. K. Tremper et al, *Anesthesiology*, Vol. 70, No. 1 (1989) pp. 98–108.

SUMMARY OF THE INVENTION

In contrast to prior art hematocrit analysis techniques, the present invention provides a method and apparatus for noninvasive hematocrit determination using a first-order electrical approximation of whole blood wherein hematocrit is ascertained via two-frequency electrical impedance measurement. The approximation is based on the premise that there is both an extracellular and an intracellular path for current passing through blood, the former being characterized by a frequency-independent resistance, and the latter by both a frequency-independent resistance and a frequency-dependent capacitance, the cell membrane of red blood corpuscles being predominantly capacitive in nature. At low frequencies the measured impedance of blood will be attributable to the plasma component, and at higher frequencies, to both plasma and red cells, the volume of red cells affecting the magnitude of the capacitive-response and thus the magnitude of the impedance response of the blood.

In practicing the present invention, impedance is measured via application of stimulation and sensor electrodes to a portion of the body that contains a pulsating vascular compartment such as an artery. For the sake of convenience, the electrodes are usually applied to a finger or limb. The stimulation electrodes are driven with a constant alternating current composite waveform comprising two frequencies, and the sensor electrodes measure voltage at those frequencies, the envelope of the measured voltage at each frequency being directly proportional to the tissue impedance at those frequencies. The sensed signals are sent into two amplitude modulation (AM), or signal envelope, detectors, and the resulting signals are converted to the digital domain by an analog to digital (A/D) converter for subsequent processing and display.

As the impedances measured by the sensor electrodes represent not only that of the blood within the vascular compartment, but include those of all of the intracellular and extracellular components of the extremity under test, it is necessary to isolate the impedance response attributable to the blood within the vascular compartment from that of the surrounding tissue in order to determine the hematocrit. This isolation is effected by concentrating on the relatively diminutive pulsatile component of the detected voltage envelope signals, either by use of a high resolution analog to digital converter to attain adequate definition of the pulsatile component of the signal, or by setting a voltage clamp level at the baseline voltage, subtracting, magnifying and then digitizing the remaining signal using an analog to digital converter of lesser resolution. The highly resolved, or clamped and magnified, pulsatile signal component at each of the two frequencies is extracted over an identical time period by a suitable processing means and normalized. The two normalized pulsatile component segments are then formed into a ratio which is representative of the hematocrit, and the ratio utilized as an index to a look-up table of corresponding hematocrit values which has been constructed from clinical studies. In practice, it is preferable to repeatedly extract a series of time-matched low and high frequency pulsatile component segments over time and form a like plurality of ratios. The ratios are then averaged by employing an averaging technique which more heavily weights ratios formed from pulsatile segments having values changing more rapidly with time than those with smaller relative changes, and the weighted ratio average correlated to an hematocrit value. This continuous process, from extraction of digitized pulsatile component segments to display of hematocrit, is preferably performed and controlled by a suitably programmed, general purpose microcomputer.

Thus, the present invention provides the medical practitioner with an accurate means and method for noninvasively determining hematocrit virtually instantaneously and on a substantially continuous basis.

BRIEF DESCRIPTION OF THE DRAWINGS

The present invention will be more fully understood by one of ordinary skill in the art through a review of the following detailed description of the preferred embodiments in conjunction with the accompanying drawings, wherein.

DETAILED DESCRIPTION OF THE PREFERRED EMBODIMENTS

Figure 1:
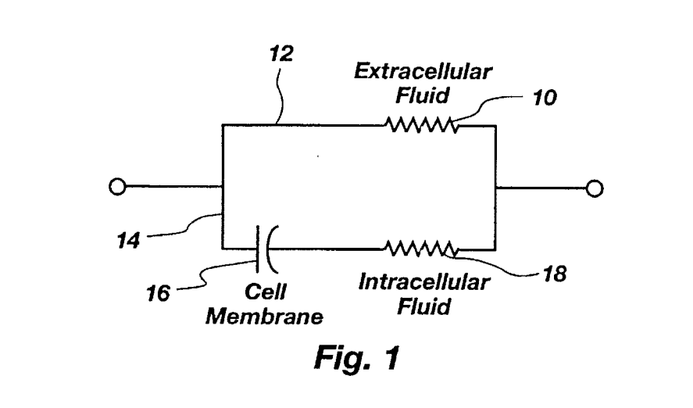
FIG. 1 comprises a circuit schematic for a first-order electrical approximation of whole blood.

FIG. 1 of the drawings depicts an approximation of the behavior of whole blood when subjected to an alternating electrical current, resistance 10 in circuit path 12 representing the response of the extracellular or plasma component, while the parallel circuit path 14, representative of the erythrocyte or red blood corpuscle component, includes both a capacitance 16 as well as a resistance 18. At low frequencies (such as 50 KHz), whole blood impedance is attributable primarily to the extracellular blood component circuit path 12, while at higher frequencies (for example, 1 MHz) the capacitive nature of the cell membrane of the red blood corpuscles results in a more significant impedance contribution from circuit path 14, reducing the magnitude of the whole blood impedance. Thus, in simplified terms, the ratio of a low frequency impedance to a high frequency impedance is representative of the relative volume percent of red blood corpuscles, or hematocrit. There is no precise frequency or narrow band at which the red cell capacitance phenomenon becomes significant, but rather a transition zone of frequencies over which the capacitive component increases in a relatively rapid manner. As will be explained in more detail hereafter, the impedance magnitude differential due to the frequency response characteristics of blood below and above the aforementioned transition zone enables the practitioner employing the present invention to utilize electrical stimulation of the patient to determine hematocrit in a noninvasive manner. However, in order to make use of frequency-based impedance differentials in whole blood to determine hematocrit, it is necessary to remove the dominant body tissue impedance component of the body portion through which impedance is measured.

Figure 6:
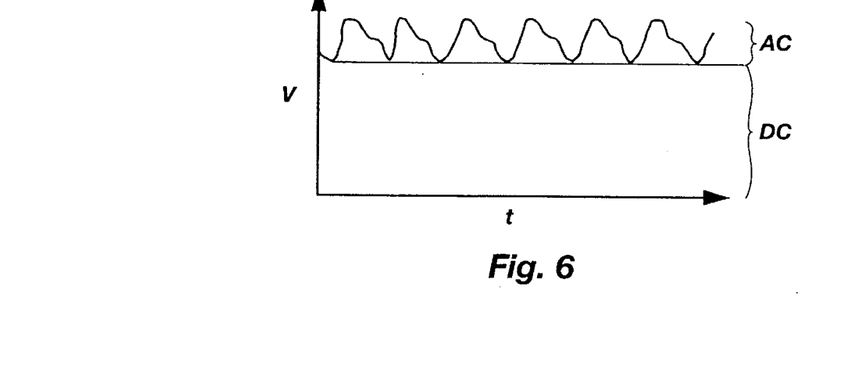
FIG. 6 comprises a graphic, not to scale depiction of an analog voltage signal representative of those measured in practicing the present invention showing the relatively small pulsatile component of the signal above the signal baseline.

FIG. 6 of the drawings comprises a representative sector of a demodulated voltage signal envelope over a period of time as measured by sensors attached to an electrically stimulated extremity of a patient according to the present invention, the measured voltage being directly proportional to and therefore representative of the total impedance of the whole blood plus the surrounding tissue. As shown, the signal envelope includes a dominant DC or baseline component and a small AC or pulsatile component. The DC component is generated by the patient's tissue, non-pulsatile arterial blood, and venous and capillary blood of the stimulated body portion. The AC component is attributable only to the pulsatile blood, and is therefore truly representative of whole blood impedance for a given frequency. AC components at different frequencies will have substantially identical voltage envelope shapes, differing only in magnitude due to the aforementioned frequency-dependent nature of the whole blood impedance response. By isolating and utilizing only the AC, or pulsatile, component of the signal, the impedance effects of the patient's extravascular tissue are eliminated and a hematocrit determination may be made using the ratio of a low frequency pulsatile impedance to a high frequency pulsatile impedance.

Figure 2:
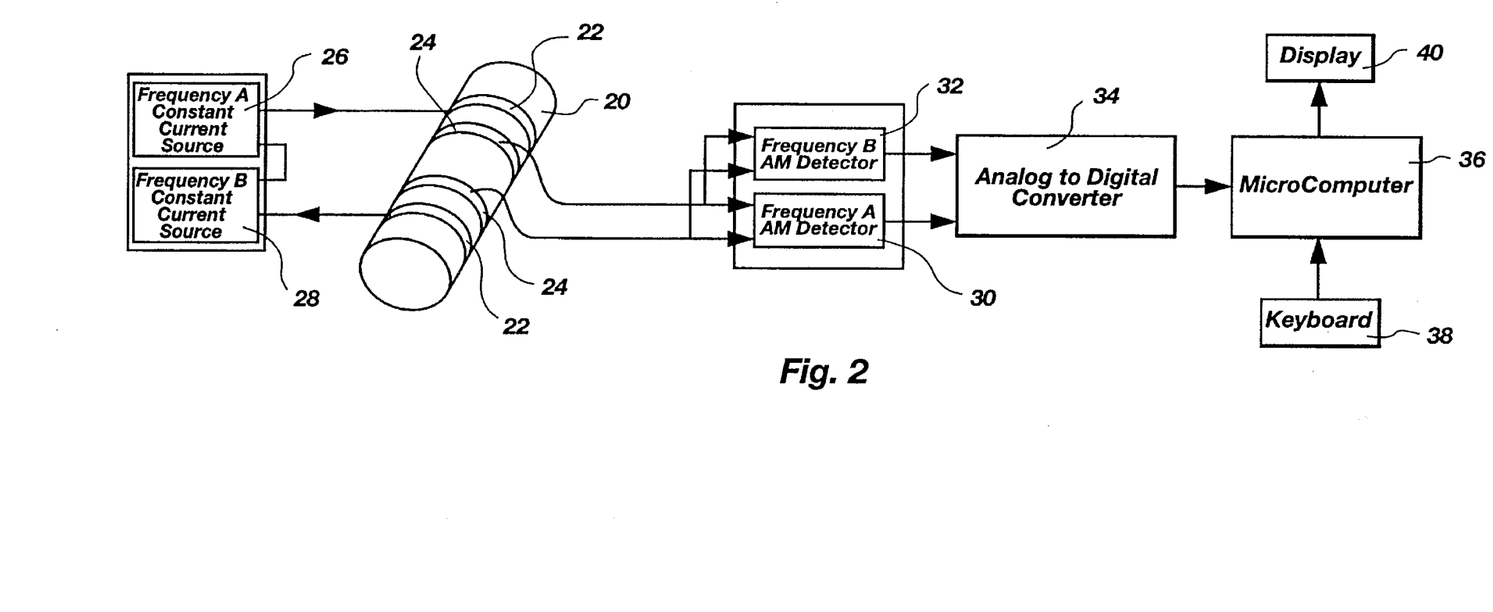
FIG. 2 comprises a combined block diagram and schematic of a preferred-embodiment of the apparatus of the present invention, with electrodes applied to a patient extremity.

FIG. 2 shows a patient body portion 20 containing an artery (which may also be referred to as a pulsatile vascular compartment), on the exterior of which have been placed outer stimulation electrodes 22 and inner sensor electrodes 24, all of which are preferably ring electrodes so as to envelop the body portion 20. The four electrode method is a standard engineering technique which helps to eliminate errors attributable to contact resistance and, except insofar as it is employed in the preferred embodiment of the present invention, does not constitute a part thereof.

Power or stimulation electrodes 22 are driven with a constant current composite carrier waveform consisting of two frequencies A and B provided by current sources 26 and 28. It is preferred that the applied constant current be of a peak-to-peak magnitude of 2 mA or less. Frequencies A and B should differ sufficiently to provide a significantly different blood impedance response to each frequency due to the capacitive component of the patient's blood, and thus an impedance differential useful in practicing the present invention. It has been found that a low frequency A of 50 KHz and a high frequency B of 1 MHz provide a good differential response, in that they are, respectively, sufficiently far below and above the frequency transition zone wherein the capacitive component of the response becomes significant. It should be noted at this point that use of frequencies much below 50 KHz is inadvisable for reasons of patient safety, in that lower frequencies may induce heart arrythmia.

Each frequency excites the tissue of body portion 20 with a constant current, and the resulting voltage signal at each frequency is measured from inner sensor electrodes 24. Since the current excitation is constant, the envelope of the measured voltage at each frequency is directly proportional to the tissue impedance at that frequency. AM Detectors 30 and 32, one each for frequency A and frequency B, measure the envelope of the voltage signals, and transmit the resulting signals to A/D Converter 34, which converts the signals to the digital domain for isolation of the pulsatile component of the signal and further processing by a programmed processing unit, preferably general purpose Microcomputer 36, in response to commands from Keyboard 38. Microcomputer 36 repeatedly extracts time-matched converted pulsatile signal component segments at each frequency, normalizes them against the voltage baseline of the respective carrier waveforms and then creates a series of segment ratios of the normalized pulsatile signal components. These ratios are averaged, preferably using a weighted averaging methodology which more heavily weights more significant ratios, being those comprised of pulsatile component segments exhibiting the greatest change in voltage magnitude over time. The weighted average of the ratios is representative of the hematocrit, the latter being extracted from an internal look-up table of corresponding ratio and hematocrit values by Microcomputer 36, and displayed to the practitioner via Display 40, which may comprise a graphic screen display, a numerical display, or both.

Figure 3:
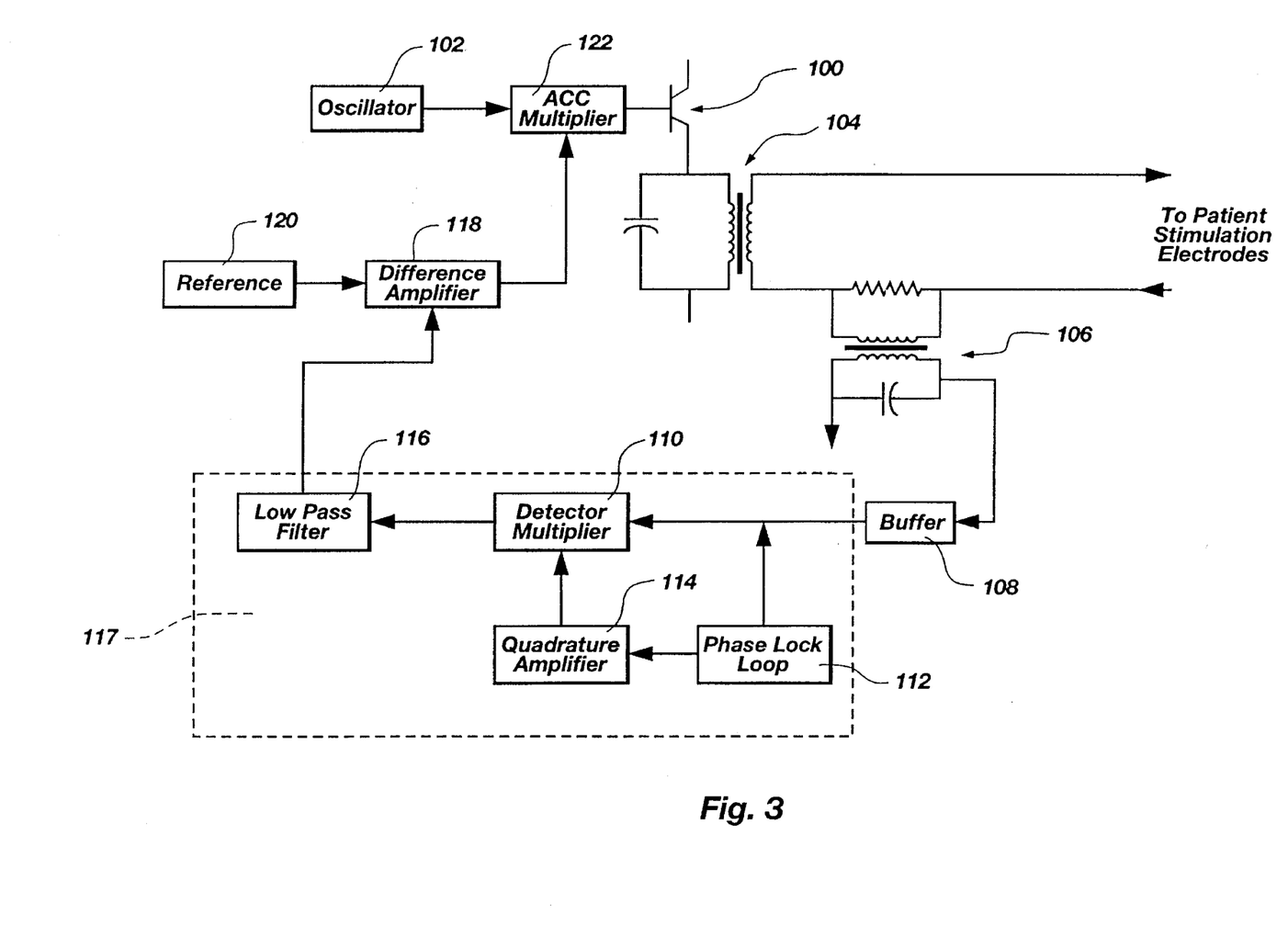
FIG. 3 comprises a schematic of a preferred embodiment of a constant current source as employed in the apparatus of the present invention.

The preferred embodiment of current sources 26 and 28, as depicted in FIG. 3, uses transistor 100 as an approximation of a current source, which is driven by oscillator 102 through automatic gain control (AGC) multiplier 122 at the desired frequency, the resulting output signal driving power transformer 104 which in turn outputs to patient stimulation electrodes 22. Isolation of each current source using transformer coupling via power transformer 104 and pickoff transformer 106 is used for patient safety. It should be noted that, as is well known in the art, transformers 104 and 106 should be wound to maximize their response at the frequencies of interest and minimize sensitivity to artifact. A sensing or regulator signal is picked off from the output coil of transformer 106 and transmitted through buffer 108 to phase lock loop synchronous AM detector 117, which includes detector multiplier 110, phase lock loop 112, quadrature amplifier 114 and low pass filter 116. Phase lock loops are well known in the art, as are AM synchronous detectors incorporating same, and therefore their structure and function will not be further described herein. However, a brief but excellent description of phase lock loops, their operation, versatility and applications, specifically in the fabrication of an AM synchronous detector suitable for use with the present invention, appears in the 1987 *EXAR Databook*, pp. 6–62 through 65 and 11–68 through 71, published by EXAR Corporation, 2222 Qume Drive, San Jose, Calif. 95131. Detector 117 outputs the envelope of the sensed current drive signal to difference amplifier 118 for comparison to the input signal from reference 120, the output signal from difference amplifier 118 controlling AGC multiplier 122, the output of which is impressed with the desired frequency (A or B) by oscillator 102. Thus a servo-control loop to maintain a substantially constant output from the current source is established. Current sources 26 and 28 are substantially identical except for the frequencies dictated by oscillators 102.

Figure 4:
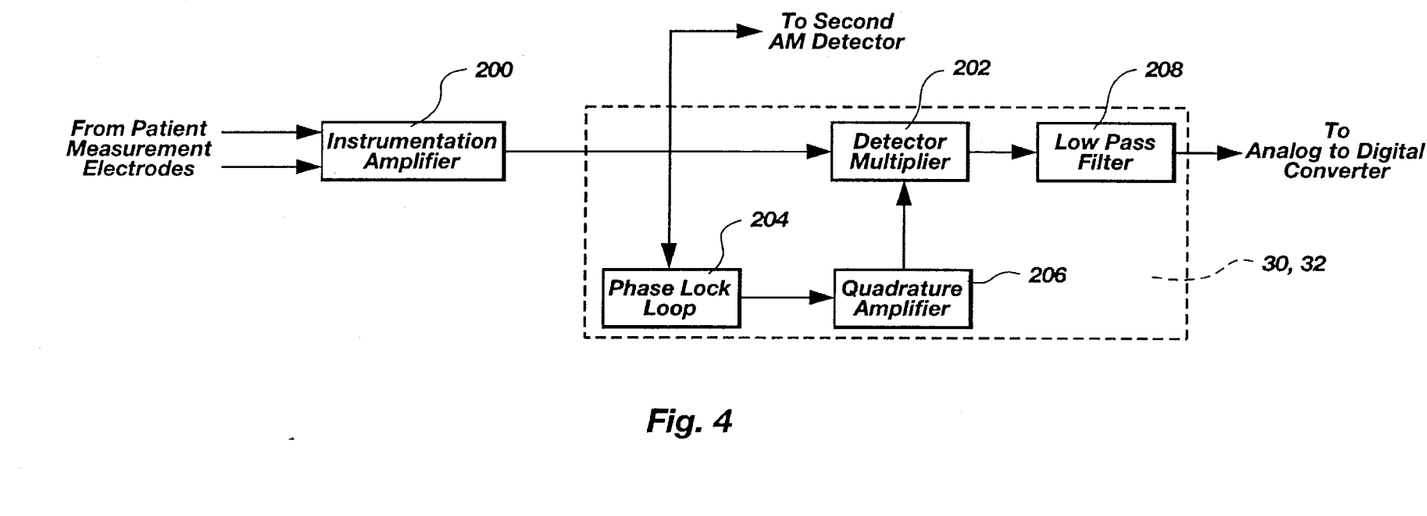
FIG. 4 comprises a schematic of a preferred embodiment of an AM detector as employed in the apparatus of the present invention.

The AM Detectors 30 and 32 used in the present invention, as depicted in FIG. 4, are AM synchronous detectors built around a phase lock loop. The measured voltage signal from the sensor or patient measurement electrodes 24, which is quite minute, is amplified by instrumentation amplifier 200 and sent to detector multiplier 202 and phase lock loop 204 of each AM Detector 30 and 32, the output of the phase lock loops being filtered by low pass filters 208. The outputs of Detectors 30 and 32 are thus the envelopes of the measured voltage waveforms at low and high frequencies, respectively, and inherently representative of impedance at those frequencies. As noted previously, phase lock loops and synchronous AM detectors, their structure and function are well known in the art, and the reader is again referred to the above-referenced pages of the 1987 *EXAR Databook* for a more detailed description thereof.

Figure 5:
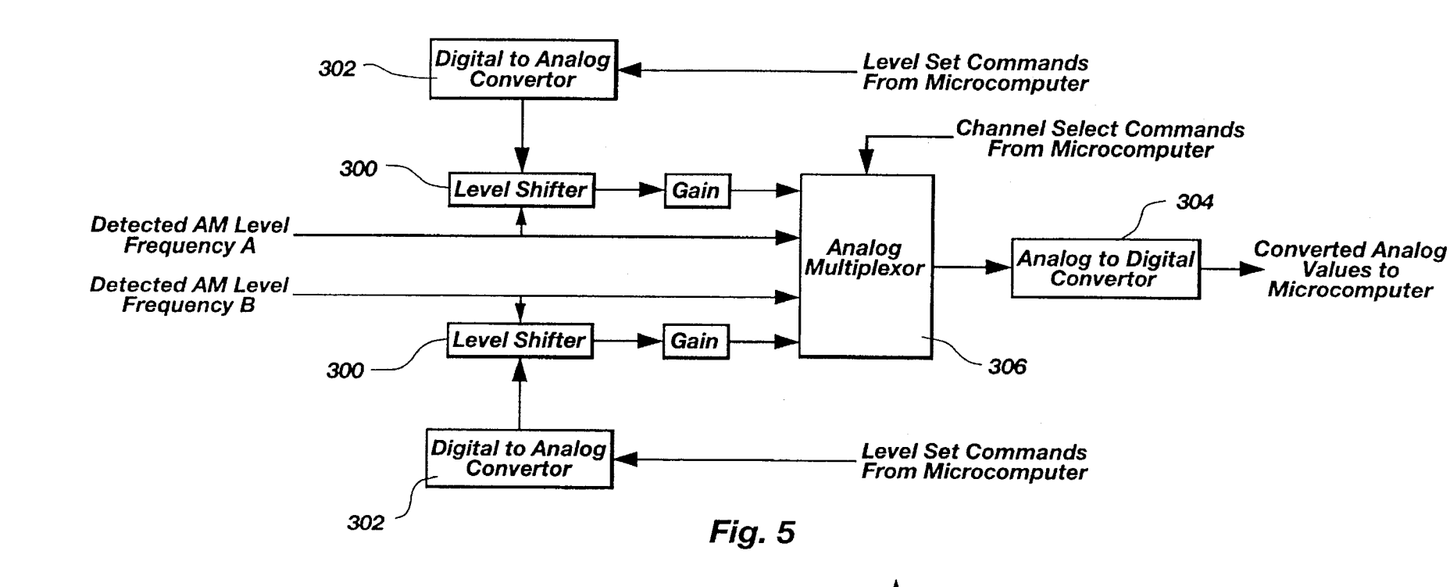
FIG. 5 comprises a schematic of a preferred embodiment of an A/D converter as employed in the apparatus of the present invention.

The demodulated voltage signal envelopes from AM Detectors 30 and 32 are received by A/D Converter 34, depicted in its preferred embodiment in FIG. 5, A/D Converter 34 including a pair of level shifters 300, each driven by level set commands from Microcomputer 36 via digital to analog (D/A) convertors 302 to extend the range of high resolution analog to digital (A/D) converter unit 304 to accommodate the fact that the variable (pulsatile) component of the impedance being measured typically constitutes only about one percent (1%) of the total measured impedance. Analog multiplexor 306 selects the appropriate signals from either AM Detector 30 or 32 responsive to channel select commands from Microcomputer 36, and feeds the selected signal to analog to digital converter unit 304 for conversion to the digital domain.

One preferred means of obtaining the pulsatile waveform component of interest in the practice of the present invention is to utilize a high resolution A/D converter unit 304, that is to say one which has a 20–22 bit resolution capability, and digitize the entire waveform, including both the small AC (pulsatile) and much larger DC (baseline) components. This provides a sufficiently large dynamic range so that the pulsatile, or AC component, of the waveform at each frequency can be isolated to provide meaningful data. However, this approach requires a relatively expensive A/D converter unit, and an alternative approach is to set a voltage clamp level at the magnitude of the DC component, subtract this from the waveform and magnify the remaining signal. The voltage clamp approach is less expensive as it requires fewer bits of resolution capability in the A/D converter unit.

Segments of the converted analog values from Detectors 30 and 32 are then repeatedly extracted over identical time periods by Microcomputer 36, correlated to further reduce noise effects, and then normalized by dividing by the voltage baseline of their respective carrier waveforms before a series of ratios of the time-matched digitized pulsatile component signal segments at frequencies A and B are calculated. The ratios are averaged in the preferred embodiment using weighted averaging techniques well known in the art, relative weighting being based upon the change in voltage magnitude versus time for the time period over which the digitized signals are extracted. Stated another way, the greater the $\Delta V$ per $\Delta t$ for a pair of time-matched component segments, the more significant the resulting ratio and the more heavily the ratio is weighted in the averaging process. The weighted ratio average, which is representative of hematocrit, is correlated to a hematocrit value by Microcomputer 36 via a look-up table of corresponding ratio and hematocrit values constructed a priori from clinical studies and depicted numerically and/or graphically to the practitioner on Display 40. Of course, the foregoing process from measurement of voltage across the patient body portion 20 to ultimate output of patient hematocrit on Display 40 is performed repeatedly and substantially continuously, so that variations and trends in hematocrit will be immediately apparent. The use of empirical data for the look-up table is due to the fact that the electrical approximation employed for the whole blood model is first-order, and a rigorous derivation of the response of the model will be inaccurate. Moreover, any such derivations will yield calibration results which vary with the two frequencies chosen, as well as the gain factors of the various stages of the apparatus.

As will be evident to the skilled practitioner of the art, all components of the apparatus utilized to practice the present invention should be selected for low noise output, due to the extremely low signal magnitude of the signal of interest.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed.

I claim:

1. An apparatus for noninvasive determination of the relative volume percent of erythrocytes, also termed the hematocrit, of whole blood having an impedance, comprising:

means for producing a constant current at first low and second high carrier wave frequencies, said first low frequency being below a frequency zone within which said erythrocytes significantly affect the magnitude of the impedance of said whole blood, and said second high frequency being within said frequency zone;

means for stimulating a patient body portion including a pulsatile vascular compartment containing said whole blood with said first low and second high frequency current;

means for sensing voltage at each of said first low and second high carrier wave frequencies across said stimulated patient body portion;

means for detecting a signal envelope of each of said sensed voltages, each of said detected signal envelopes having a pulsatile component and a baseline component;

means for isolating the pulsatile component of each of said detected signal envelopes;

processing means for extracting at least one set of time-matched segments of said isolated pulsatile signal envelope components, creating a ratio from said isolated time-matched pulsatile signal envelope component segments of said at least one set, and for correlating said ratio to said hematocrit.

2. The apparatus of claim 1, wherein said processing means includes means for normalizing said isolated pulsatile signal envelope component segments before creating said ratio.

3. The apparatus of claim 1, further including means for digitizing at least a portion of said isolated pulsatile signal components of said detected signal envelopes prior to said creation of said ratio.

4. The apparatus of claim 3, further including means for eliminating said baseline components of said detected signal envelopes prior to the digitizing thereof by said digitizing means.

5. The apparatus of claim 4, further including means for magnification of said isolated pulsatile signal envelope components after said elimination of said baseline components.

6. The apparatus of claim 1, further including means for digitizing said detected signal envelopes in their entirety for isolation of said pulsatile components therefrom.

7. The apparatus of claim 3, wherein said digitizing means comprises an analog to digital converter.

8. The apparatus of claim 7, wherein said analog to digital converter includes means for altering a range of said isolated signal components responsive to commands from said processor means.

9. The apparatus of claim 8, wherein said analog to digital converter includes multiplexor means for selecting analog signals for conversion to the digital domain from said detector means and from said range alteration means.

10. The apparatus of claim 9, wherein said multiplexor means includes means for selecting said analog signals for digitizing responsive to commands from said processor means.

11. The apparatus of claim 1, wherein said processing means further includes means for extracting a plurality of time-matched pulsatile signal component segments at said first low and second high frequencies at intervals over a period of time, to create a plurality of said ratios therefrom, to average said plurality of ratios and to correlate said averaged ratios to said hematocrit.

12. The apparatus of claim 11, wherein said processing means, in performing said averaging, includes means for weighting significant ratios more heavily.

13. The apparatus of claim 1, wherein said detecting means comprises a first and a second AM detector, one for each of said first low and second high carrier wave frequencies.

14. The apparatus of claim 1, wherein said correlating means comprises look-up table means for correlating ratio values to hematocrit, and said created ratio is employed by said processor means as an index to said look-up table means to determine the hematocrit corresponding thereto.

15. The apparatus of claim 1, further including means for displaying the hematocrit corresponding to said created ratio.

16. A method of noninvasively determining the relative volume percent of erythrocytes, also termed the hematocrit, of whole blood having an impedance, comprising:

producing a constant current at first low and second high carrier wave frequencies, said first low frequency being below a frequency zone within which said erythrocytes significantly affect the magnitude of the impedance of said whole blood, and said second high frequency being within said frequency zone;

stimulating a patient body portion including a pulsatile vascular compartment containing said whole blood with said first low and second high frequency current;

sensing voltage at each of said first low and second high carrier wave frequencies across said stimulated patient body portion;

detecting a signal envelope of each of said sensed voltages, each of said detected signal envelopes having a pulsatile component and a baseline component;

isolating the pulsatile component of each of said detected signal envelopes; and extracting at least one set of time-matched segments of said isolated pulsatile signal envelope components, creating a ratio from said isolated time-matched pulsatile signal envelope component segments of said at least one set, and correlating said ratio to said hematocrit.

17. The method of claim 16, further including the step of normalizing said isolated pulsatile signal envelope component segments before creating said ratio.

18. The method of claim 16, further including the step of digitizing at least a portion of said isolated pulsatile signal components of said detected signal envelopes prior to said creation of said ratio.

19. The method of claim 16, further including the step of eliminating said baseline components of said detected signal envelopes prior to the step of digitizing.

20. The method of claim 19, further including the step of magnifying said isolated pulsatile signal envelope components after said elimination of said baseline components.

21. The method of claim 18, further comprising digitizing said detected signal envelopes in their entirety for isolation of said pulsatile components therefrom.

22. The method of claim 16, comprising extracting a plurality of time-matched pulsatile signal component segments at said first low and second high frequencies at intervals over a period of time, creating a plurality of ratios therefrom, averaging said plurality of ratios and correlating said averaged ratios to said hematocrit.

23. The method of claim 22, wherein significant ratios are weighted more heavily in said averaging thereof.

24. The method of claim 16, wherein said step of correlating further comprises:

providing a look-up table correlating ratio values to hematocrit; and using said created ratio as an index to said look-up table to determine the hematocrit corresponding thereto.

25. The method of claim 16, further including the step of displaying the hematocrit corresponding to said created ratio.

26. An apparatus for determination of the relative volume percent of erythrocytes, also termed the hematocrit, of whole blood having an impedance, comprising:

means for producing a constant current at first low and second high carrier wave frequencies, said first low frequency being below a frequency zone within which said erythrocytes significantly affect the magnitude of the impedance of said whole blood, and said second high frequency being within said frequency zone;

means for applying said first low and second high frequency current to a volume of whole blood;

means for sensing voltage at each of said first and second carrier wave frequencies across said volume; and processing means for creating a ratio from said sensed voltages, and for correlating said ratio to said hematocrit.

27. The apparatus of claim 26, wherein said volume of said whole blood is flowing and said processing means includes means for extracting a plurality of time-matched segments of said sensed voltages over a period of time, to create a plurality of said ratios therefrom, to average said plurality of ratios and to correlate said averaged ratios to said hematocrit.

28. The apparatus of claim 27, wherein said processing means, in performing said averaging, includes means for weighting significant ratios more heavily.

29. The apparatus of claim 26, wherein said correlating means comprises look-up table means for correlating ratio values to hematocrit, and said created ratio is employed by said processor means as an index to said look-up table means to determine the hematocrit corresponding thereto.

30. The apparatus of claim 26, further including means for displaying the hematocrit corresponding to said created ratio.

* * * * *

UNITED STATES PATENT AND TRADEMARK OFFICE
CERTIFICATE OF CORRECTION

PATENT NO. : 5,526,808
DATED : June 18, 1996
INVENTOR(S) : Kaminsky

It is certified that error appears in the above-indentified patent and that said Letters Patent is hereby corrected as shown below:

On the title page, first column, under "U.S. PATENT DOCUMENTS", 14th patent down, change "Graveinstein" to --Gravenstein--;

On the title page, second column, under "OTHER PUBLICATIONS", line 5, change "plethysmegraph" to --plethysmograph--;

On page 2, first column, line 5, change "impedancer" to --impedances--;

On page 2, first column, line 9, change "466" to --465--;

On page 2, first column, line 10, change "plethyamography" to --plethysmography;

On page 2, first column, line 17, change "haemodialysia" to --haemodialysis--;

On page 2, first column, line 25, change "plethyomoraph" to --plethysmograph--;

On page 2, second column, line 1, change "plethysmegraph" to --plethysmograph--;

On page 2, second column, line 17, change "184" to --1984--;

On page 2, second column, line 19, change "pestoperative" to --postoperative--;

On page 2, second column, line 28, change "plethyomograph" to --plethysmograph--;

UNITED STATES PATENT AND TRADEMARK OFFICE
CERTIFICATE OF CORRECTION

PATENT NO. : 5,526,808
DATED : June 18, 1996
INVENTOR(S) : Kaminsky

It is certified that error appears in the above-indentified patent and that said Letters Patent is hereby corrected as shown below:

In Column 3, line 1, change "capacitive-response" to --capacitive response--;

In Column 3, line 67, change "preferred-embodiment" to --preferred embodiment--;

In Column 9, line 40, change "16" to --18--; and

In Column 9, line 49, after "16," insert --further--.

Signed and Sealed this

Seventeenth Day of December, 1996

Attest:

BRUCE LEHMAN

Attesting Officer

Commissioner of Patents and Trademarks